United States Patent [19]
Munshi et al.

[11] Patent Number: 5,411,537
[45] Date of Patent: May 2, 1995

[54] RECHARGEABLE BIOMEDICAL BATTERY POWERED DEVICES WITH RECHARGING AND CONTROL SYSTEM THEREFOR

[75] Inventors: Mohammed Z. Munshi, Missouri City; Ashok P. Nedungadi, Lake Jackson, both of Tex.

[73] Assignee: Intermedics, Inc., Angleton, Tex.

[21] Appl. No.: 145,945

[22] Filed: Oct. 29, 1993

[51] Int. Cl.⁶ .............................................. A61N 1/00
[52] U.S. Cl. ................................. 607/33; 320/22; 320/38; 320/40
[58] Field of Search ............................ 607/9, 33, 34; 320/22–24, 38, 40

[56] References Cited

U.S. PATENT DOCUMENTS

| | | | |
|---|---|---|---|
| 3,195,540 | 7/1965 | Waller | 128/422 |
| 3,454,012 | 7/1969 | Raddi | 128/422 |
| 3,688,177 | 8/1972 | Reeves et al. | 320/24 |
| 3,824,129 | 7/1974 | Fagan, Jr. | 136/6 R |
| 3,867,950 | 2/1975 | Fischell | 128/419 P |
| 3,888,260 | 6/1975 | Fischell | 128/419 PG |
| 3,942,535 | 3/1976 | Schulman | 128/419 PS |
| 4,014,346 | 3/1977 | Brownlee et al. | 128/419 PS |
| 4,082,097 | 4/1978 | Mann et al. | 128/419 PS |
| 4,096,866 | 6/1978 | Fischell | 128/419 PG |
| 4,134,408 | 1/1979 | Brownlee et al. | 128/419 PS |
| 4,172,459 | 10/1979 | Hepp | 128/697 |
| 4,275,739 | 6/1981 | Fischell | 128/419 PS |
| 4,432,363 | 2/1984 | Kakegawa | 128/419 PS |
| 4,661,107 | 4/1987 | Fink | 623/2 |
| 4,665,896 | 5/1987 | LaForge et al. | 128/1 D |
| 4,941,472 | 7/1990 | Moden et al. | 128/419 PS |
| 5,237,259 | 8/1993 | Sanpei | 320/23 |
| 5,279,292 | 1/1994 | Baumann et al. | 607/137 |

*Primary Examiner*—William E. Kamm
*Assistant Examiner*—Marianne Parker
*Attorney, Agent, or Firm*—John R. Markling

[57] ABSTRACT

An improved hermetically-sealed automatic implantable cardioverter-defibrillator (AICD) or any other bioimplantable device which may be operated on a single rechargeable cell, or a dual power source system, the rechargeable component being recharged by magnetic induction. Included in the implantable devices are new lithium rechargeable chemistries designed to sense the state-of-charge or discharge of the battery; a battery charge controller specifically designed to recharge a lithium battery rapidly to less than 100% full charge, and preferably 90%, more preferably 80%, of full rated charge capacity; and charging means for multi-step charging. The batteries are based on lithium chemistries specially designed to yield higher currents than conventional primary lithium chemistries and to permit long-term performance despite sub-capacity recharging.

49 Claims, 5 Drawing Sheets

RECHARGEABLE BIOMEDICAL BATTERY POWERED DEVICES WITH RECHARGING AND CONTROL SYSTEM THEREFOR

FIELD OF OUR INVENTION

Our invention is directed towards a rechargeable battery-powered biomedical device such as a cardiac pacemaker or a cardioverter-defibrillator, incorporating a rechargeable lithium power source, a battery charge controller designed for recharging, monitoring, and controlling the state of the lithium power source, and for fast charging of the rechargeable lithium power source without overcharging, and particularly to less than 100% of full theoretical charge capacity, preferably to no more than 90% of charge capacity and more preferably to about 80% of charge capacity.

BACKGROUND OF OUR INVENTION

Electrically driven implantable devices are used principally as cardiac pacemakers, but they have also been considered for heart assist systems, drug infusion and dispensing systems, defibrillators, nerve and bone growth stimulators, gut stimulators, pain suppressors, scoliosis treatment apparatus, artificial vision apparatus, artificial hearts, artificial larynxs, bladder stimulators, brain stimulators, muscle stimulation, and implanted sensors.

The basic pacemaker system consists of an electrode attached to the heart and connected by a flexible lead to a pulse generator. This generator is a combination of a power source and the microelectronics required for the pacemaker system to perform its intended function. A fixed rate pacemaker provides continuous pulses to the heart, irrespective of proper heart beating, while a demand inhibited pacemaker provides pulses only when the heart fails to deliver a natural pulse. Depending upon the various sensed events, the pacemaker stimulates the right atrium, the right ventricle, or both chambers of the heart in succession. The pacemakers in current use incorporate circuits and antennae to communicate noninvasively with external instruments called programmers. Most of today's pacemakers are of the demand inhibited type, hermetically sealed, and programmable.

Early pacemakers were powered by primary zinc-mercuric oxide cells. Although this system was used for about 15 years, it did suffer from high self-discharge and hydrogen gas evolution. Several mechanisms contributed to battery failure, most of them related to the chemistry of the cell. In addition, the open-circuit voltage of each cell was only 1.5 V per cell and several cells had to be connected in series to obtain the required voltage for pacing. Furthermore, the pacemaker could not be hermetically sealed due to the gas evolution, and had to be encapsulated in heavy epoxy. In 1970, the average life of the pulse generator was only 2 years, and 80 percent of explants were necessitated by failed batteries.

Consideration was given to many means of power generation and power storage. This included primary chemical batteries of all sorts, nuclear batteries, rechargeable batteries, and the separation of the stimulator system into two parts, with the power pack being outside the patient's body and transmitting pulses of energy to a passive implanted receiver and lead. Cardiac pacemakers based on rechargeable nickel-cadmium systems (1.2 V per cell) and rechargeable zinc-mercuric oxide systems (1.5 V per cell) were developed. Such pacemakers are described in prior art references, including U.S. Pat. Nos. 3,454,012; 3,824,129; 3,867,950; 3,888,260; and 4,014,346. The rechargeable pacemaker incorporated a charging circuit which was energized by electromagnetic induction, or other means. This produced a current in the charging circuit which was made to flow to the rechargeable battery. Although this system was incorporated in many cardiac pacemakers, it was unpopular among patients and physicians primarily because the frequency of the recharges was too high (weekly), and the nickel-cadmium system suffered from memory effects which reduced the battery capacity exponentially after each recharge. In addition, the specific energy density of both types of rechargeable batteries was poor, the call voltages were low, there was no clear state-of-charge indication, and hydrogen gas liberated during overcharge was not properly scavenged either through a recombination reaction, or hydrogen getters.

One of the problems in charging a nickel-cadmium cell or a zinc-mercuric oxide call is that they have a fairly flat voltage-time curve, and hence poor state-of-charge or discharge indication. Overcharged nickel-cadmium cells liberate oxygen exothermically at the nickel electrode which migrates to the cadmium electrode and recombines to form cadmium hydroxide. In some cases, this is a poor charge indication since for fast charge, the rate of oxygen evolution may be higher than the rate of oxygen recombination, and cells may not reach full charge, leading to an excess of gas pressure and cell venting. The overcharge reaction involves a slight heating of the cell which lowers its cell voltage. It is this $-\Delta V$ which is used quite commonly in commercial nickel-cadmium chargers to determine full charge of nickel-cadmium cells.

Other means of controlling the recharging operation have also been used. For example, U.S. Pat. No. 3,775,661 teaches that the pressure buildup internally can be sensed by a diaphragm that is external to the battery. As the pressure within the cell casing increases, the diaphragm is flexed to actuate an associated switch connected in the battery charging circuitry, deenergizing the charger when the battery internal pressure indicates a fully charged state.

U.S. Pat. No. 4,275,739 uses a diaphragm internal to the cell and the deflection of this diaphragm during internal pressure increase indicates the cell reaching full charge.

U.S. Pat. No. 3,824,129 suggests using a "stabistor" connected in parallel to the cell such that when the cell voltage approaches or reaches the fully charged level, the stabistor diverts the charge current, and stops call charging. This approach does not lead to efficient means of charging or provide adequate safety for nickel-cadmium or zinc-mercuric oxide calls since both cells exhibit a fairly flat charge voltage and the end-of-charge indication is poor. Hence, cells may evolve gas which may go undetected before the stabistor diverts the current.

In U.S. Pat. No. 3,942,535 an implanted cardiac pacemaker is described in which the charging current is monitored and a signal, whose frequency is related to the current amplitude, is transmitted external to the patient. The patent further describes an electrical shunt regulation in the charging circuit to prevent excessive voltage and current from being applied to the rechargeable cell. In U.S. Pat. No. 3,888,260 similar means are described. These patents do not control the amount of charging and the problems of gas evolution described above may arise.

U.S. Pat. No. 4,082,097 describes a system for controlling the charge of a battery, and a battery protection device designed to sense the state of charge and limit the charging amplitude. A pressure switch is incorporated whose function is to provide a signal to the circuitry when the battery reaches a preselected charge state. In addition, an undefined electrode is incorporated that provides an output voltage whose amplitude is related to the state of charge of the battery. The function of this electrode is to sense any parameter that changes with the state of charge.

The only rechargeable systems available at the time of these patents were those based on conventional chemistries, such as nickel-cadmium, lead-acid, etc., and these cells only evolve gas close to their full charge levels. Hence, the pressure switch could only be functional at or close to the charged state. Furthermore, since gas evolution was not a true function of the state of charge, the electrode incorporated to provide a voltage change or sense some parameter could not also be functional.

Today, most nickel-cadmium chargers utilize different means to control and cease battery charging. The end-of-charge indicators for such calls can be maximum voltage, maximum time, maximum temperature, a negative $\Delta V$, $dV/dt$, $\Delta T$, or $dT/dt$. The details of these end-of-charge indicators can be found in EDN, May 13, 1993.

Both zinc-mercuric oxide or the nickel-cadmium cells, the previous battery system for rechargeable battery heart or body stimulators, suffered from problems such as memory effects, and high self-discharge. Fast recharge could only be accomplished if the battery was fast-charged to some preselected voltage followed by a trickle charge. It was well known that nickel-cadmium batteries that are fast charged cannot be charged to 100 percent of rated cell capacity. This loss of capacity is due to what is called a memory effect. Each time the battery is discharged at some low current rate, and charged at a higher current rate, the loss in capacity accumulates. Such cells then have to be fully discharged and "reconditioned" before the full capacity can be recovered. Because of this capacity loss and also loss due to high self-discharge, the patient had to have the pacemaker recharged every week. The rechargeable battery pacemakers were developed for lifetimes of over 10 years. Yet, because of the battery chemistry, they only lasted 2 or 3 years, which was the same lifetime as that of primary cells at that time.

It is desirable therefore, to incorporate a battery system in a bioimplantable device such as a cardiac pacemaker or a defibrillator, that overcomes many of the previous problems. The desirable battery parameters should include a high cell voltage, long cycle life, high discharge rate capability, high charge rate capability, no memory effect, no gas evolution, non-toxic chemicals in the battery, high energy density, ability to shape the battery in various configurations, low self-discharge, proper state-of-charge indication, and improved reliability. In addition, the charge control of the battery needs to be properly controlled in order to prolong the life of the battery and to minimize recharge time.

SUMMARY OF OUR INVENTION

We have invented a pacemaker or a defibrillator or any other bioimplantable battery-powered device incorporating either a single rechargeable power source, or a dual system power source comprised of primary and secondary power sources wherein the rechargeable (secondary) power source is recharged through the patient's skin by electromagnetic induction from either an A.C. or a D.C. source. A single rechargeable power source could be used for either a uni-function device such as a cardiac pacemaker or a multifunction implantable cardioverter/defibrillator (ICD). However, the dual system power source is intended only for a multifunction device such as an ICD, wherein the primary power source would power a low-power consumption application such as bradycardia pacing, and the rechargeable power source would be used for a demand-only application, such as high-energy cardioversion/defibrillation. The advantages of such rechargeable battery-operated systems as described in this patent include: (1) The device can be made significantly smaller, lighter, and thinner than present designs; (2) The cardioverter-defibrillator device can be pectorally implanted while the small size and lightweight pacemaker device can be used for smaller patients such as children; (3) If the cardioverter-defibrillator device can is used as an electrode, then this "hot can" replaces the presently incorporated subcutaneous patch electrode, and this has clear clinical and physiological advantages; (4) Single cell devices avoid potential mismatch problems associated with the use of a series connected string of batteries (hence greater reliability); (5) The battery can be cycle tested for reliability prior to assembly in the medical device (primary cells cannot be tested and high rate use may result in increased battery failure); (6) Certain chemistries described in this invention have a much higher current carrying capacity (high rate capability) without loss in performance compared to primary cells; (7) Many of the chemistries described in this invention have a high cut-off voltage per cell (greater than 2.4 volts per cell); (8) The cells have very high open-circuit voltages (3.5–4.1 V); (9) The device has been realistically projected to have a longevity of greater than 20 years, which would result in lower costs in the long run; (10) The cells have excellent and reliable state-of-charge and discharge indications; (11) The use of a thin film battery construction results in the ability to charge the battery faster with greater reliability; (12) A safety switch is built into the cell that terminates the current to prevent the cell from venting, expanding, and overheating; (13) The cells need only be charged every 6–18 months, instead of weekly charges carried out previously using nickel-cadmiums batteries; (14) Many cell chemistries described in this invention have a good shelf-life (1–3 percent per year); and (15) The cells can be hermetically sealed.

We have also invented a control system that can accurately monitor the state-of-charge of the rechargeable cell, more specifically, a rechargeable lithium cell. Proper monitoring of the charge control is important to prolong the life of the battery. The control circuitry will allow the patient or physician to know exactly what the state-of-charge is of the cell simply by measuring its voltage. The control circuitry controls the amplitude of the current depending upon its state-of-charge. The charging will be via duty cycling so that for a preset time every second, part of the time is used for monitoring the battery's voltage and hence its state-of-charge. The invention also describes a means of multi-step fast charging the lithium cells, in order to reduce the time of charge and charge more efficiently.

We will now describe our preferred embodiment of our invention, in connection with the accompanying drawings.

DESCRIPTION OF OUR PREFERRED INVENTION

Figure 1:
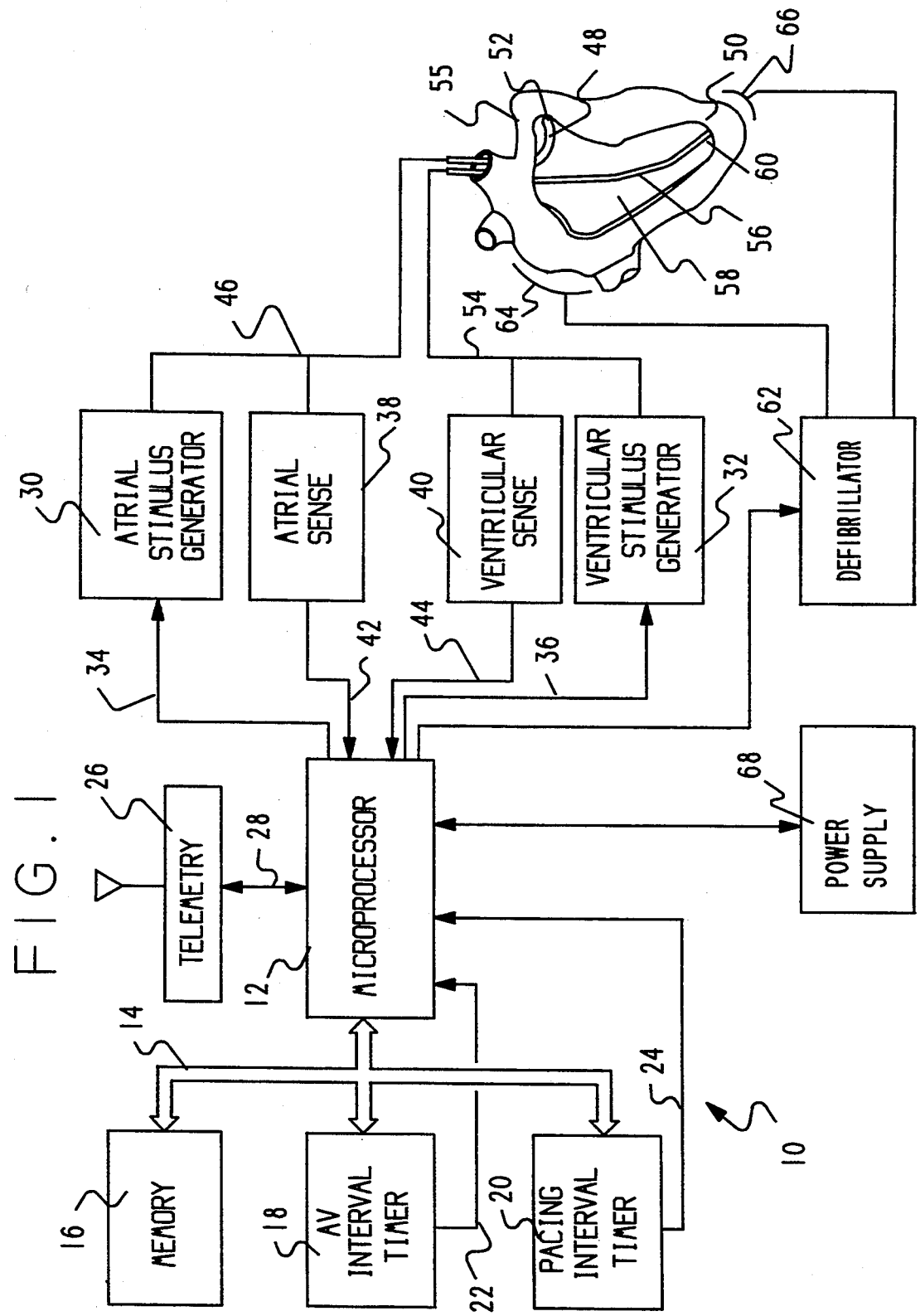
FIG. 1 is a block diagram of an implantable pacemaker/defibrillator with rechargeable power supply.

FIG. 1 is a block diagram illustrating a rate adaptive pacemaker/defibrillator 10 according to our invention. A microprocessor 12 preferably provides pacemaker control and computational facilities. It will be appreciated that other forms of circuitry, such as analog or discrete digital circuitry can be used in place of microprocessor 12. However, a microprocessor is preferred for its miniature size and its flexibility, both of which are of critical importance in the implantable systems in which it is envisioned the invention will find use. A particularly energy efficient microprocessor which is designed specifically for use herein is fully described in Gordon, et al, U.S. Pat. No. 4,404,972, which is also assigned to our assignee and the disclosure thereof is incorporated herein by reference.

The microprocessor 12 has input/output ports connected in a conventional manner via bidirectional bus 14 to memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively.

Memory 16 preferably includes both ROM and RAM. The microprocessor 12 may also contain additional ROM and RAM as described in the Gordon, et al. U.S. Pat. No. 4,404,972. The pacemaker operating routine is stored in ROM. The RAM stores various programmable parameters and variables.

The A-V and pacing interval timers 18 and 20 may be external to the microprocessor 50, as illustrated, or internal thereto, as described in the Gordon, et al. U.S. Pat. No. 4,404,972. The timers 18, 20 are suitable conventional up or down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22, 24.

The microprocessor 12 preferably also has an input/output port connected to a telemetry interface 26 by line 28. The pacemaker when implanted is thus able to receive pacing and rate control parameters from an external programmer and send data to an external receiver if desired. Many suitable telemetry systems are known to those skilled in the art. One such system and encoding arrangement is described in Calfee, et al. U.S. Pat. No. 4,539,992 which is also assigned to our assignee. That description is incorporated herein by reference.

The microprocessor 12 output ports are connected to inputs of an atrial stimulus pulse generator 30 and a ventricle stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines.

The microprocessor 12 also has input ports connected to outputs of an atrial sense amplifier 38 and a ventricular sense amplifier 40 by lines 42 and 44 respectively. The atrial and ventricular sense amplifiers 38, 40 detect occurrences of P-waves and R-waves. The atrial sense amplifier 30 outputs a signal on line 42 to the microprocessor 12 when it detects a P-wave. This signal is latched to the microprocessor 12 input port by a conventional latch (not shown). The ventricular sense amplifier 40 outputs a signal on line 44 to the microprocessor 12 when it detects an R-wave. This signal is also latched to the microprocessor 12 input port by a conventional latch (not shown).

The input of the atrial sense amplifier 38 and the output of the atrial stimulus pulse generator 30 are connected to a first conductor 46, which passes through a conventional first lead 48. Lead 48 is inserted into a patient's heart 50 intravenously or in any other suitable manner. The lead 48 has an electrically conductive pacing/sensing tip 52 at its distal end which is electrically connected to the conductor 46. The pacing/sensing tip 52 is preferably lodged in the right atrium 54.

The input of the ventricular sense amplifier 40 and the output of the ventricular stimulus pulse generator 32 are connected to a second conductor 54. The second conductor 54 passes through a conventional second lead 56 which is inserted intravenously or otherwise in the right ventricle 56 of the heart 50. The second lead 56 has an electrically conductive pacing/sensing tip 60 at its distal end. The pacing/sensing tip 60 is electrically connected to the conductor 54. The pacing/sensing tip 60 is preferably lodged on the wall of the right ventricle 58.

The conductors 46, 54 conduct the stimulus pulses generated by the atrial and ventricular stimulus pulse generators 30, 32 respectively, to the pacing/sensing tips 52, 60. The pacing/sensing tips 52, 60 and corresponding conductors 46, 54 also conduct cardiac electrical signals sensed in the right atrium and right ventricle to the atrial and ventricular amplifiers, 38, 40 respectively. The sense amplifiers 38, 40 enhance the electrical signals. In the preferred embodiments of our invention, the amplifiers 38, 40 have an automatic gain control feature, as described in U.S. Pat. No. 4,903,699 to Baker, et al. That application is assigned to the same assignee as our present invention, and the disclosure thereof is incorporated herein by reference.

The implantable cardiac stimulator 10 may also have a defibrillator circuit 62. If fibrillation is detected through the atrial or ventricular sense amplifiers 38, 40, a high energy shock can be delivered through defibrillation electrodes 64, 66. Detection algorithms for detection of tachycardias and fibrillation are described in Pless, et al, U.S. Pat. No. 4,880,005. Although patch-type electrodes 64, 66 are suggested, endocardial electrodes for defibrillation are also known.

All of the aforementioned components are powered by a power supply 68. The supply 68 may comprise both primary and rechargeable batteries, which may be dedicated to the operation of different parts of the stimulator 10. We will now describe our inventive rechargeable power supply.

The rechargeable batteries, suitable for use in our invention, are based on a number of different types of lithium chemistries. A rechargeable lithium battery (Type I) consists of a lithium anode, a liquid organic solvent/lithium salt electrolyte absorbed in a separator material, and a composite cathode consisting essentially of the active cathode, a carbon additive to impart electronic conductivity (such as graphite, shawinigan black, or acetylene black), and a binder to hold the active cathode together. The active cathode can be selected from a wide range of oxides, sulfides, or selenides, such as, $MnO_2$, $LiMn_2O_4$, $Li_xMnO_2$, $MoS_2$, $MoS_3$, $MoV_2O_8$, $CoO_2$, $Li_xCoO_2$, $V_6O_{13}$, $V_2O_5$, $V_3O_8$, $VO_2$, $V_2S_5$, $TiS_2$, $NbSe_3$, $Cr_2O_5$, $Cr_3O_8$, $WO_3$, $Li_xNiO_2$, etc. These Type I lithium battery systems generally have a self-discharge of generally less than one percent per year, thus prolonging longevity. Two such chemistries, namely, the $U/MoS_2$ and the $U/MnO_2$ systems have been commercialized to some extent by Moll Energy (Canada).

The second type of lithium battery (Type II) also incorporates a lithium anode and an active cathode of a type similar to those described above, but utilizes an ionically conducting polymer electrolyte as the backbone to immobilize the liquid organic solvent/lithium salt composition. The polymer electrolyte also acts as a separator. Thus there is no need for an additional separator. The polymer electrolyte phase is also incorporated in the composite cathode to impart ionic conductivity and also provide added flexibility. The polymer for the polymer electrolyte generally consist of a radiation, heat, or chemical curable polymer and may incorporate a liquid organic solvent. The use of the solvent in the polymer matrix leads to a more highly conductive polymer than a polymer without the solvent. Hence, batteries constructed of polymer electrolytes without the organic solvent in the polymer generally have a low discharge rate. In addition, this approach would lead to the construction of very thin film batteries, an advantage in the field of implantable devices.

The third type of lithium battery (Type III) incorporates a lithium intercalating carbon anode ($Li_xC$) and a lithiated composite cathode. The electrolyte can be either of the conventional rechargeable lithium battery type (Type I), or of the polymer electrolyte battery type (Type II). This system is also termed the lithium-ion system. The lithiated cathode is generally $Li_xMn_2O_4$, $Li_xNiO_2$, or $Li_xCoO_2$. Graphitic carbon anodes have been evaluated as negative electrodes because they offer chemical stability, improved cycle life, and added safety compared to lithium metal cells. These carbons have layered graphitic structures in which the lithium can be intercalated. Such cells have recently been commercialized by Sony Energytec for consumer applications. One of the advantages of $Li_xC$ composite negative electrodes over metallic lithium is that no metallic lithium is generated, which enhances the safety of the rechargeable battery—a plus for bioimplantable operation. Another advantage is that unlike conventional lithium cells, these cells deliver a considerably higher number of cycles without much capacity degradation. The number of cycles for a conventional lithium battery is only about 200 cycles, whereas that for a lithium ion cell is as high as 1200 cycles. The disadvantages include a slight decrease in the energy density compared to that of a pure lithium anode cell, and a higher level of self-discharge (10–12%/month or 45%/year for $Li_xCoO_2$; 2–3%/month or 20%/year for $Li_xNiO_2$). Cells based on $Li_xNiO_2$ would work very well with a low-level of self-discharge. In addition, these cells have a higher voltage level (4.2 V) compared to conventional lithium batteries (3.6 V). In many cases, a single cell is all that is required. This will also eliminate the problems associated with a series string of cells.

Figure 4:
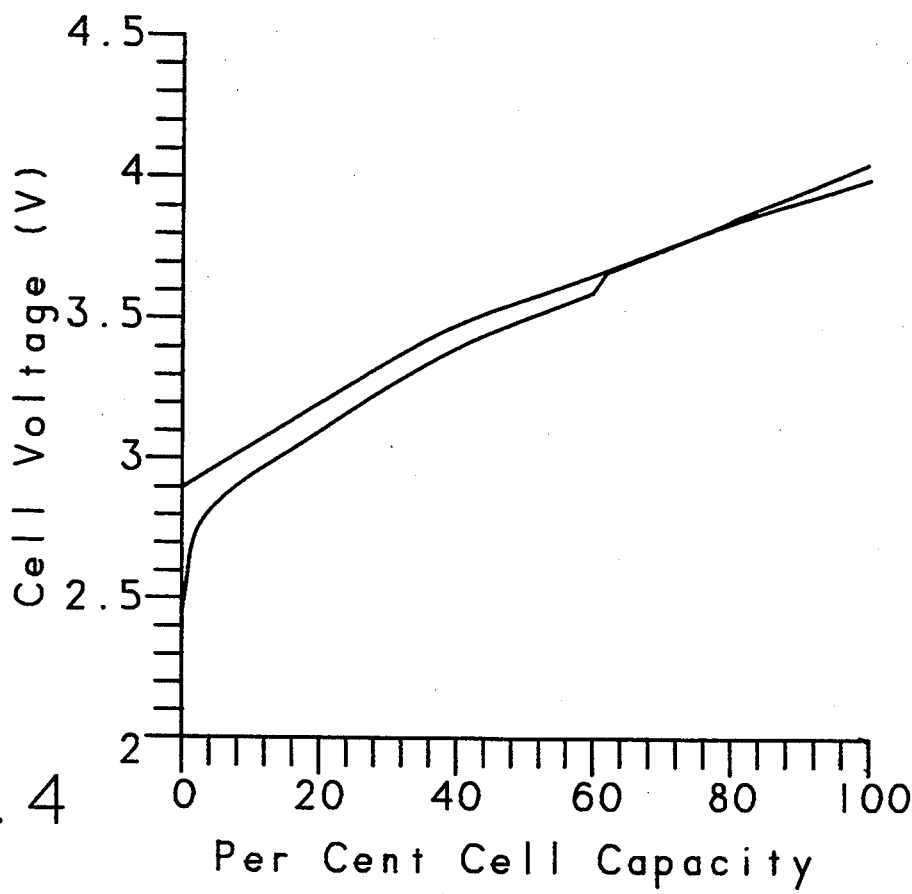
FIG. 4 is a graph of percent cell capacity to voltage for a representative battery.

All of the batteries described above (Types I, II, or III) exhibit a relatively linear relationship between the state of charge of the battery and the cell voltage. This is illustrated in FIG. 4. FIG. 4 shows a representative plot of percent cell capacity or state-of-charge to cell voltage for a Type III battery, specifically a lithiated cobalt oxide battery ($Li_xCoO_2$). During charging the upper line of the graph would be more representative of the relationship between the capacity and the voltage. During discharging, on the other hand, the cell voltage sags a little bit, producing the lower line of the graph. The displacement of these two lines from each other has been slightly exaggerated to illustrate the distinction mentioned above. The relationship shown in FIG. 4 is typical of the batteries heretofore described. Thus, a measurement of the open circuit voltage of the battery can be correlated to the state of charge of the cell or battery.

Figure 5:
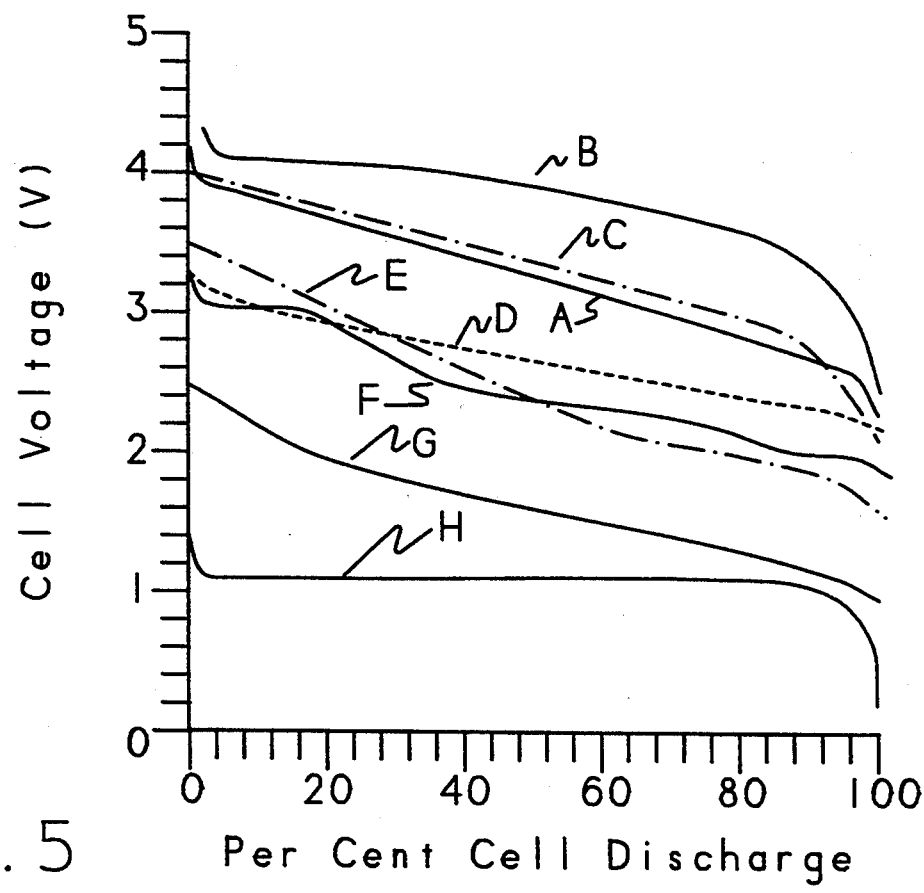
FIG. 5 is a graph of percent cell capacity to voltage for selected battery chemistries.

This phenomenon is also illustrated in FIG. 5 which shows curves for selected cathode types for lithium batteries and a conventional nickel cadmium Ni-Cd rechargeable battery. FIG. 5 plots percent cell discharge against cell voltage. Percent cell discharge is the compliment of the percent cell capacity; in other words, 100% cell capacity is 0% discharge. The lithiated cobalt oxide battery ($Li_xCoC_2$) is shown at A. A $Li_xMn_2O_4$ a cathode battery is graphed at B. A $Li_xNiO_2$ is graphed at C. A similar cathode for $Li_{1+x}V_3O_8$ is shown at E. The titanium sulfide cathode ($TiS_2$), labeled G, indicates the lower cell voltage of this type of battery. Line E is representative of a $V_6O_{13}$ cathode. In addition to the overall characteristic of this type battery, this battery also demonstrates several small plateaus, which would make the relationship between the cell state-of-charge and the cell voltage less precise. In contrast to all of these batteries, a standard nickel cadmium cell is plotted at H. It can be seen that the curve H for the nickel cadmium battery is much flatter throughout most of the cell discharge.

Figure 6:
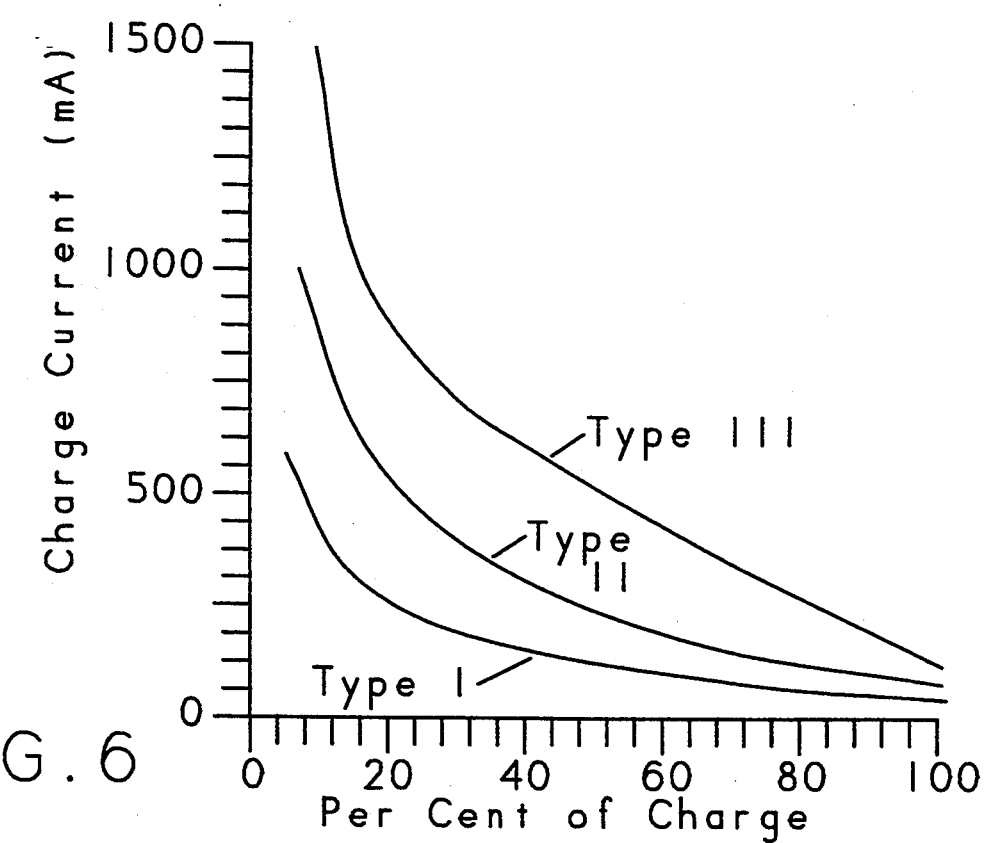
FIG. 6 is a graph of percent charge to charge current representative of three types of batteries described herein.

When a battery of any of the aforementioned types, I, II, or III is recharged, the acceptable charging current is also related to the state of charge. As the state of charge increases, the effective amount of current which can be accepted by the battery decreases. This relationship is shown in FIG. 6. For all three types of batteries, a representative curve is illustrated. Our invention utilizes these characteristics to optimize the charging of the battery. By periodically testing the open circuit voltage of the battery during charging, the state-of-charge can be estimated and the appropriate charging current level can be selected. Using this technique, the battery can be recharged more quickly than with standard techniques.

Figure 7:
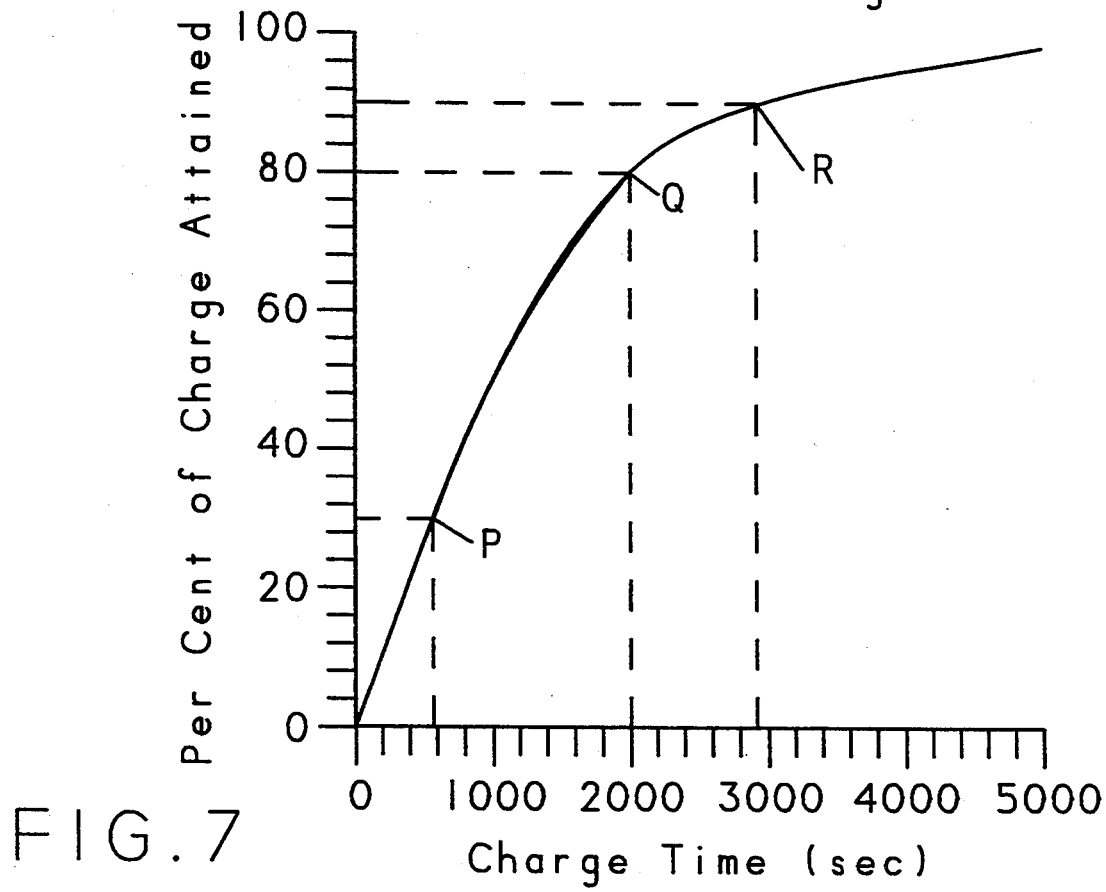
FIG. 7 is a representative graph of charge time to percent of rated charge attained.

This relationship is illustrated in FIG. 7 which shows a typical graph of charge time in seconds to the percent rated charge obtained. 100% is the full rated charge of the battery. It can be seen from FIG. 7 that initial charging is relatively quick and that the curve flattens out after about 80% of charge, extending to a total charge time on the order of 5000 seconds. Of course, the battery should not be completely discharged in a pacemaker type apparatus. In this application, a signal for recharging would be generated before the complete discharge of the battery, preferably at about 30% of the rated charge of the battery or point P in FIG. 7. Because of the changing slope of the curve illustrated in FIG. 7, most of the charge can be restored to the battery in a shorter time if the battery is charged to less than its full rated capacity. Thus, if the battery is charged to 90% of its capacity at point R, a time saving of almost 50% over an attempt to charge to full rated capacity. Similarly, if the battery is charged to 80%, point Q on the graph, the total charge time (between P and Q) is about 25 to 30% of the time required to charge from point P all the way to the rated maximum charge. Thus, a significant gain can be achieved with little loss of battery capacity. This advantage is made possible by the ability to test periodically the state-of-charge and the lack of memory effects in the selected batteries.

Compared to Type I or II, Type III has a more predictable and pronounced state-of-charge discharge indication or intrinsic end-of-service indication. Nevertheless,. FIG. 5 shows that for Type I, Type II and Type III batteries, the voltage of the cell has a direct relationship with capacity in a linear manner, and this feature can be used to monitor the capacity of the battery at any point in time simply by measuring the cell voltage. This feature did not exist with previous rechargeable pacemaker cells. Type I and II can also be tailored to have a particular sloping voltage by selecting an appropriate cathode. In fact, most of the insertion compounds used as cathode materials for Type I and II systems have a sloping voltage.

In current bradycardia pacemakers, a primary $Li/I_2$ battery is used by nearly all manufacturers of cardiac pacemakers. This system has been shown to be extremely reliable with increased longevity compared to other primary-based systems. However, in order to reduce the size of the device even further, a rechargeable lithium power source needs to be incorporated instead. Simulation studies have shown that a Type I, II, or III secondary battery should provide adequate capacities for a constant bradycardia pacing operation of at least one year before a recharge is necessary; a projected longevity of significantly greater than 25 years; and weigh only 6-8 grams (present pacemaker cells weigh 12-25 grams). This would result in a total weight reduction of greater than 20% of the current pacemaker. These types of pacemakers that are lightweight and considerably smaller than present designs would be ideal for smaller patients such as children. In fact, for child patients, the battery size and hence the final size of the pacemaker or any other medical device could be reduced even further if the frequency of the recharging could be increased to one every six months.

The implantable device 10 incorporates bradycardia pacing, anti/tachycardia pacing, low-energy cardioversion, and high-energy cardioversion/defibrillation. Simulation studies for a single "AA" size cell of Types I, II, or III (18 grams / 8 cm$^3$) for continuous bradycardia pacing and twelve full defibrillation shocks a year indicate that all three battery types are capable of providing adequate energies to function up to one year before a recharge is necessary. The capacity remaining at the end of the year can be anywhere from 60 to 77% depending upon the system. A lithium ion system utilizing a $Li_xNiO_2$ cathode has about 20% self-discharge a year whereas a Type I lithium rechargeable system has a self-discharge of less than 2% per year. Even if more shocks are required, both systems have adequate reserve capacities to sustain the demand. Using this approach, the size of the batteries can be reduced by about 50% compared to existing systems.

Figure 2:
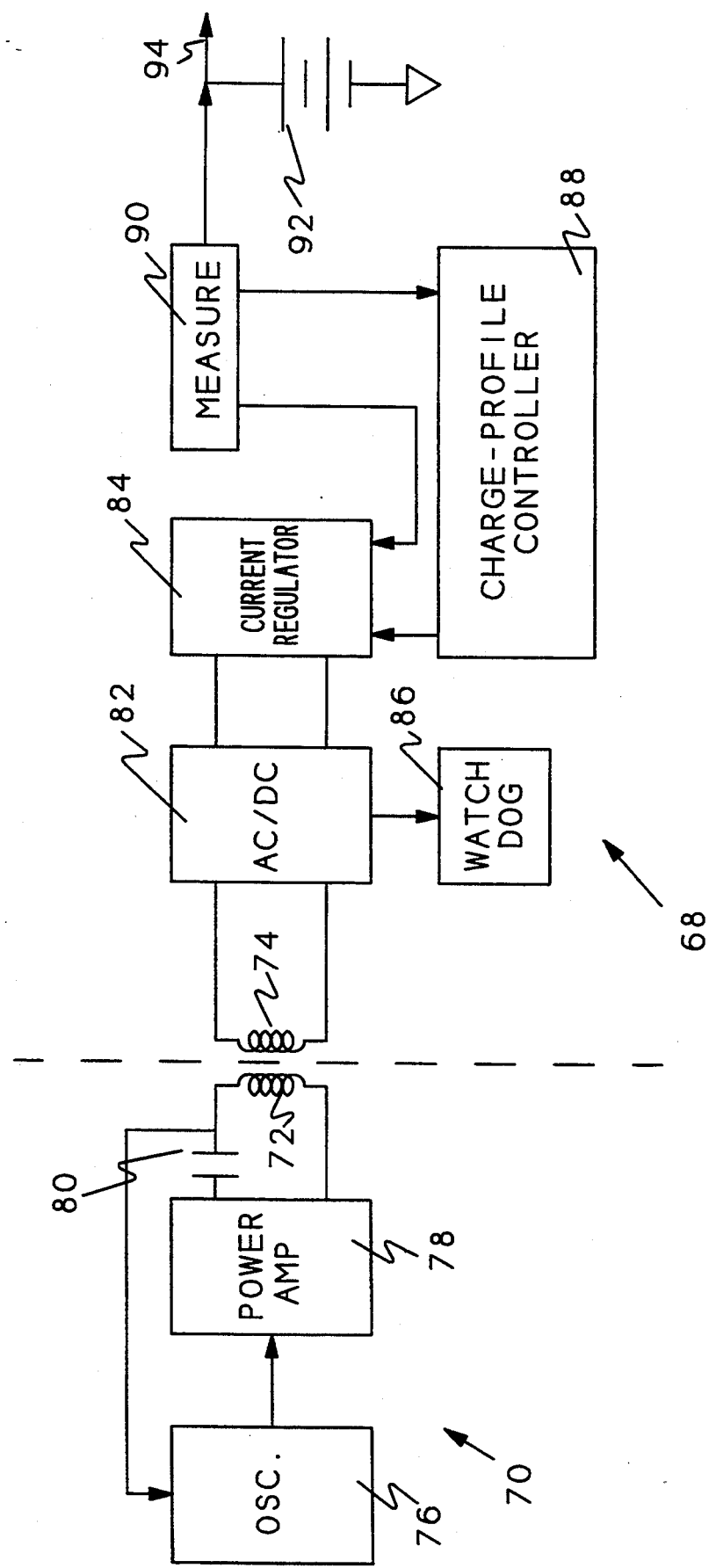
FIG. 2 is a block diagram of the rechargeable power supply.

A block diagram of the power supply 68 is shown in FIG. 2. Numerous descriptions on energy transfer by magnetic inductions are cited in many of the patents cited above on rechargeable body stimulators. For simplification, a single battery is shown. However, if a dual system power source is used, then the circuit can be modified so that only the rechargeable cell is recharged. An external charger 70 can have an A.C. or a D.C. power source. Energy for recharging the battery is coupled through the patient's skin by magnetic induction between an external charging coil 72 and an input coil 74, preferably with a ferrite core, disposed just under the skin. The external charger 70 utilizes a frequency of 10 to 40 kHz.

The block diagram of FIG. 2 depicts an implementation of the proposed non-invasive battery charging system. Both the external charger 70 and the power supply 68 comprising an internal (implanted) receiver and battery charging system are shown. The interface between the external and implanted systems consists of a pair of mutually coupled coils 72, 74 that is used to transfer electromagnetic energy from the external transmitting coil 72, through the body tissue, to the implanted receiving coil 74 by way of mutual induction.

As shown in FIG. 2, the external charger 70 consists of an oscillator circuit 76 that drives the transmitting coil 72 with an alternating current. The signal from the oscillator circuit 76 is amplified by a power amplifier 78 which is coupled through a capacitor 80 to the external transmitting coil 72. Power may be supplied to these circuits from any suitable source, such as an AC source or a DC source or battery pack. A rechargeable external battery pack with its own charging system could be provided to allow portability of the external unit. If desired, an AC-to-DC converter and regulator, together with a local charging controller could allow a user to recharge the external battery pack by connecting the system to a standard AC line outlet.

On the receiving side, the system consists of an AC-to-DC convertor 82 for converting the induced AC voltage on the receiving coil 74 to DC, an efficient current regulator 84 that regulates the charging current supplied to the implantable rechargeable battery, a watch dog circuit 86 to detect the effective presence of the external charger 70, and a charge-profile controller 68 that dynamically adjusts the implantable charging system to ensure optimal and efficient charging of the battery as more fully described below. Also included are means for measuring the battery voltage. A rechargeable lithium battery 92 is connected to the above described circuitry. A connection 94 is also provided from the rechargeable battery 92 to the other circuits of the implantable device 10. The watch dog circuit 86 detects the presence or absence of the external charger 70 permitting the power supply 68 to begin charging.

Because lithium batteries exhibit a linear relationship between state-of-charge and voltage the lithium battery in the device can be recharged using a multistep fast charge program. Multistep charging can be a very user-friendly system. The currents can be either programmed by the physician or automatically selected by the control circuitry depending upon the battery's state-of-charge condition. For example, if a rechargeable call of 400 mAh has been depleted by 50 percent, then one needs to put back in 200 mAh capacity. One could start the multistep fast charge with a first charge step of 500 mA current to a preselected voltage level. Once this level is reached, the next step could be 250 mA to a preselected level. The next current level could be 150 mA, then 100 mA and so on. This is depicted in FIG. 4. The preselected voltage could be close to the full charge voltage. Between each current step, charging can be suspended for a few seconds in order to measure the battery's open-circuit voltage, and hence its state-of-charge. Controlling the charging in this manner assures that no gas evolution or overcharging will occur.

Using this method of charging, one can charge up the cell faster and more efficiently than conventional two step charging where a single step fast charge is applied to some voltage level followed by a constant current trickle charge. The latter procedure could be not only inefficient, but could take a much longer time to charge the cell. The multistep charge process dumps a high current followed by incrementally lower currents reducing not only the time of charging but increasing the efficiency. For patients visiting the doctor's office, the charging time needs to be as small as possible. Studies have shown that the lithium batteries described in this patent can charge the cell up as fast as one hour. The efficiency of recharging the cell is close to 100 percent, i.e. the amount of coulombs put into the cell during charge is equal to the amount of coulombs that was depleted during the cell discharge. In order to avoid transients in the current or voltage during the current step change, one could either ramp up the current step from zero current to the required value or ramp down the current from the previous current value.

Figure 3:
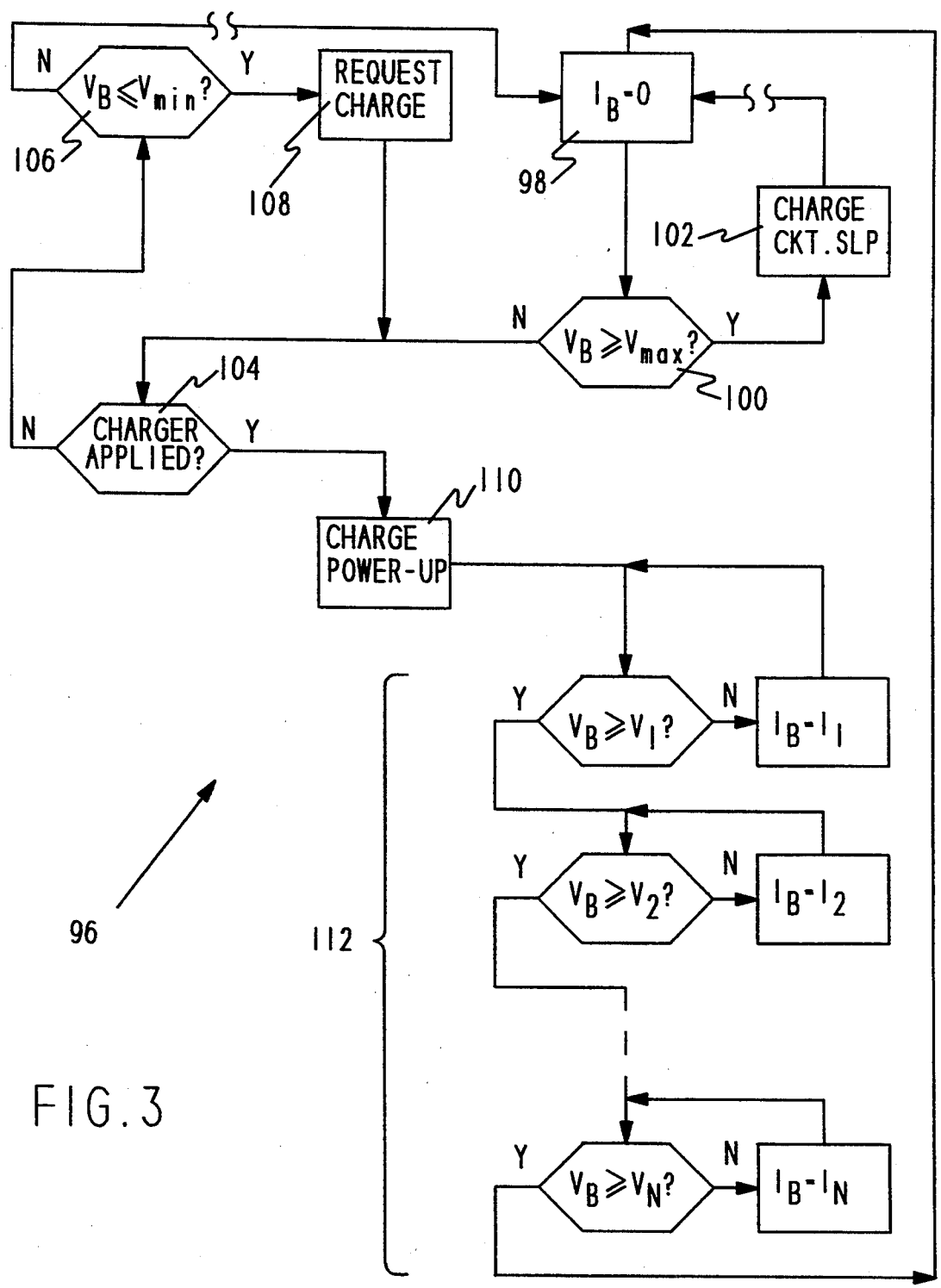
FIG. 3 is a flow chart of recharge control logic.

The charge profile controller 88 comprises a logic circuit which operates in a feedback manner to control the current being supplied to the battery 92, to optimize charging in accordance with our invention. The controller 88 may comprise analog or discrete digital circuitry, but it is preferably comprised of a state machine or a microprocessor, either independent or part of the microprocessor 12. In the controller 88, a program sequence 96, illustrated in FIG. 3, is implemented. Periodically during the operation of the implantable device 10, the open circuit voltage of the battery 92 is measured at step 98 by the measure circuit means 90. It is desired that the battery voltage remain within a predetermined range between a lower voltage $V_{min}$ and $V_{max}$. With the sampled voltage, the controller 88 checks 100 if the voltage of the battery exceeds $V_{max}$. If the voltage of the battery is greater than or equal to $V_{max}$, a charge circuit sleep sequence 102 is initiated and further data processing is provided before the controller again periodically tests at 98. In an implantable defibrillator, the test at 98 could be invoked either periodically or after a specific event, such as delivery of a shock, or both. If the voltage has fallen below $V_{max}$, the watch dog circuit is queried at 104 to determine if the external charging circuit is applied. If the charger is not applied, the controller 88 tests at 106 for the battery voltage falling below the $V_{min}$. If the battery voltage has not yet fallen equal to or below $V_{min}$, other processing continues and the charge profile controller will, at a subsequent time, again test the battery voltage at 98. If, on the other hand, the battery voltage has fallen below the predetermined $V_{min}$, a request for charge 108 will be generated and transmitted to the patient. This request for charge could take several forms. It may be latched into telemetry to be communicated with an external programmer as soon as such a device may be available. It may also be transduced into an audible or tactile signal which can be detected by the patient. If the presence of the charger is detected at step 104, the current regulator can be powered up at 110 and the battery recharge begins using a step-wise recharging pattern indicated by steps 112. In the steps 112, the current regulator is serially set to different preselected current levels 14, $I_1$, $I_2$...$I_n$. Periodically during the charging process, the battery is set to an open circuit condition so that the open circuit voltage of the battery may be measured by the measuring means 90. If the voltage of the battery $V_b$ exceeds or equals a particular predetermined level, for example $V_1$, then the current regulator continues to transfer power to the battery at a predetermined level $I_1$. When the battery voltage $V_b$ exceeds $V_1$, however, but is also less than $V_2$, the current will be regulated to $I_2$. This process will be repeated in as many steps as may be desired until the voltage exceeds a predetermined normal voltage $V_n$. Typically, the value of $V_n$ is greater than $V_{max}$.

The advantages of the proposed noninvasive charging system can be understood by considering the various operations it is designed to perform during a typical charging cycle. Initially, during normal operation of the implantable device, the battery voltage is sufficiently high to ensure safe operation of the therapeutic device. In this mode, all circuits in the implantable device related to battery charging (except for the battery voltage monitoring circuit and a watchdog circuit) are deactivated in order to conserve energy in the implantable battery. Over the course of time, due to the continuous drain by the therapeutic circuits and also partly due to self-discharge, the battery voltage decreases to a predetermined critical value which is close to but sufficiently above the point where the operating reliability of therapeutic circuits would be compromised. At this point an indicator, preferably an audio signal, is turned on intermittently to request that the user take action to recharge the battery as soon as possible. Of course, the critical battery voltage at which this happens is chosen with adequate safety margin to allow continuing reliable operation of the therapeutic device for some convenient time after this first request for battery recharging.

The user initiates the battery charging operation by placing the energy transmitting coil of the external charging unit in close proximity to the implanted coil and by turning on the excitation to the transmitting coil. The watchdog circuit within the implanted device detects the presence of the activated external charging unit by detecting the induced voltage in the implanted receiver coil, and then activates all implanted circuitry related to battery charging.

The external charger has a means for measuring the transmitted power (e.g., measuring the current through the transmitting coil) and this value is continuously displayed to the user. For a fixed transmitting frequency, voltage amplitude, and coil tuning, the current through the transmitting coil is maximized when the coupling between the two coils is the strongest. This enables the user to adjust the position of the external coil and find the optimum position of maximum energy transfer simply by noting the position at which the coil current is maximized. The external coil is then fixed by (for example, a strap, belt or velcro patch in this optimal position.

Depending on the measured battery voltage, the charge profile controller 88 selects an optimum charging current value and sets the switching current regulator 84 to this value.

We claim as our invention:

1. An implantable medical device comprising
   means for delivering a therapy to the body of a patient,
   means in electrical communication with said therapy delivering means for controlling said therapy delivering means, and
   an electrical power supply having
   a rechargeable battery in electrical communication with said therapy delivering means and said controlling means., said battery having an open circuit voltage which is a substantially linear function of a charge on said battery,
   means for receiving a charge for said battery from a power source external to the body of a patient, said charge receiving means being connected to said battery,
   means in electrical communication with said battery for detecting a battery voltage of said battery, and
   means in electrical communication with said detecting means and said charge receiving means for terminating charging whenever said voltage exceeds a predetermined level.

2. The implantable medical device according to claim 1 wherein said power supply further comprises
   means in electrical communication with said charge receiving means for regulating a recharging current being delivered to said battery during charging to a plurality of predetermined current levels; and
   means in electrical communication with said voltage detecting means and said current regulating means for selecting one of said plurality of current levels as a function of said detected battery voltage.

3. The implantable medical device according to claim 2 wherein said current level selecting means comprises
   means for defining a series of voltage ranges and
   means for selecting a particular current level whenever said detected battery voltage falls within a particular one of said voltage ranges.

4. The implantable medical device according to claim 3 wherein said series of voltage ranges is a series of contiguous ranges and wherein a particular current level associated with a particular range is an inverse function of the detected battery voltage.

5. The implantable medical device according to claim 4 wherein said therapy delivering means comprise a cardiac pacemaker.

6. The implantable medical device according to claim 4 wherein said therapy delivering means comprise a cardiac defibrillator.

7. The implantable medical device according to claim 1, 2, 3 or 4 wherein the predetermined voltage level is less than 100 per cent of a rated maximum voltage of the battery.

8. The implantable medical device according to claim 7 wherein the predetermined voltage level is less than 90 per cent of the rated maximum voltage of the battery.

9. The implantable medical device according to claim 8 wherein the predetermined voltage level is less than 80 per cent of the rated maximum voltage of the battery.

10. The implantable medical device according to claim 9 wherein said therapy delivering means comprise a cardiac pacemaker.

11. The implantable medical device according to claim 9 wherein said therapy delivering means comprise a cardiac defibrillator.

12. The implantable medical device according to claim 1, 2, 3 or 4 wherein the rechargeable battery is a lithium battery.

13. The implantable medical device according to claim 12 wherein the rechargeable lithium battery comprises a lithium anode, a liquid organic solvent and lithium salt electrolyte and a composite cathode.

14. The implantable medical device according to claim 13 wherein the composite cathode comprises an active cathode, a carbon additive, and a binder.

15. The implantable medical device according to claim 14 wherein the active cathode is comprised of a substance selected from the group consisting of $MnO_2$, $LiMn_2$, $Li_xMnO_2$, $MoS_2$, $MoS_3$, $MoV_2O_8$, $CoO_2$, $Li_xCoO_2$, $V_6O_{13}$, $V_2O_5$, $V_3O_8$, $VO_2$, $V_2S_5$, $TiS_2$, $NbSe_3$, $Cr_2O_5$, $Cr_3O_8$, $WO_3$, and $Li_xNiO_2$.

16. The implantable medical device according to claim 15 wherein said therapy delivering means comprise a cardiac pacemaker.

17. The implantable medical device according to claim 15 wherein said therapy delivering means comprise a cardiac defibrillator.

18. The implantable medical device according to claim 12 wherein the rechargeable lithium battery comprises a lithium anode, an ionically conducting polymer and lithium salt electrolyte, and a composite cathode.

19. The implantable medical device according to claim 18 wherein the composite cathode comprises and active cathode, a carbon additive, and a binder.

20. The implantable medical device according to claim 19 wherein the active cathode is comprised of a substance selected from the group consisting of $MnO_2$, $LiMn_2$, $Li_xMnO_2$, $MoS_2$, $MoS_3$, $MoV_2O_8$, $CoO_2$, $Li_xCoO_2$, $V_6O_{13}$, $V_2O_5$, $V_3O_8$, $VO_2$, $V_2S_5$, $TiS_2$, $NbSe_3$, $Cr_2O_5$, $Cr_3O_8$, $WO_3$, and $Li_xNiO_2$.

21. The implantable medical device according to claim 18 wherein the electrolyte further comprises a liquid organic solvent.

22. The implantable medical device according to claim 21 wherein the composite cathode comprises an active cathode, a carbon additive, and a binder.

23. The implantable medical device according to claim 22 wherein the active cathode is comprised of a substance selected from the group consisting of $MnO_2$, $LiMn_2$, $Li_xMnO_2$, $MoS_2$, $MoS_3$, $MoV_2O_8$, $CoO_2$, $Li_xCoO_2$, $V_6O_{13}$, $V_2O_5$, $V_3O_8$, $VO_2$, $V_2S_5$, $TiS_2$, $NbSe_3$, $Cr_2O_5$, $Cr_3O_8$, $WO_3$, and $Li_xNiO_2$.

24. The implantable medical device according to claim 23 wherein said therapy delivering means comprise a cardiac pacemaker.

25. The implantable medical device according to claim 23 wherein said therapy delivering means comprise a cardiac defibrillator.

26. The implantable medical device according to claim 12 wherein the lithium battery comprises a lithium intercalating carbon anode, an electrolyte, and a lithiated composite cathode.

27. The implantable medical device according to claim 26 wherein the electrolyte comprises a liquid organic solvent and a lithium salt.

28. The implantable medical device according to claim 27 wherein said therapy delivering means comprise a cardiac pacemaker.

29. The implantable medical device according to claim 27 wherein said therapy delivering means comprise a cardiac defibrillator.

30. The implantable medical device according to claim 26 wherein the electrolyte comprises an ionically conducting polymer and lithium salt electrolyte.

31. The implantable medical device according to claim 30 wherein the electrolyte further comprises a liquid organic solvent.

32. The implantable medical device according to claim 31 wherein said therapy delivering means comprise a cardiac pacemaker.

33. The implantable medical device according to claim 31 wherein said therapy delivering means comprise a cardiac defibrillator.

34. The implantable medical device according to claim 26 wherein the lithiated cathode is comprised of a substance selected from the group consisting of $Li_xMn_2O_4$, $Li_xNiO_2$, and $Li_xCoO_2$.

35. The implantable medical device according to claim 34 wherein said therapy delivering means comprise a cardiac pacemaker.

36. The implantable medical device according to claim 34 wherein said therapy delivering means comprise a cardiac defibrillator.

37. An implantable medical device comprising
means for delivering a therapy to the body of a patient,
means in electrical communication with said therapy delivering means for controlling said therapy delivering means, and
an electrical power supply having
a rechargeable battery in electrical communication with said therapy delivering means and said controlling means,
means for receiving a charge for said battery from a power source external to the body of a patient, said charge receiving means being connected to said battery,
means in electrical communication with said battery for detecting a battery voltage of said battery, and
means in electrical communication with said detecting means and said charge receiving means for terminating charging whenever said voltage exceeds a predetermined level less than 100 per cent of a rated maximum voltage of the battery.

38. The implantable medical device according to claim 37 wherein the predetermined voltage level is less than 90 per cent of the rated maximum voltage of the battery.

39. The implantable medical device according to claim 38 wherein the predetermined voltage level is less than 80 per cent of the rated maximum voltage of the battery.

40. The implantable medical device according to claim 39 wherein said therapy delivering means comprise a cardiac pacemaker.

41. The implantable medical device according to claim 39 wherein said therapy delivering means comprise a cardiac defibrillator.

42. The implantable medical device according to claim 39 wherein said voltage detecting means further comprises means for periodically detecting said battery voltage and wherein said medical device further comprises
means for regulating a recharging current being delivered to said battery during recharging to a plurality of predetermined current levels; and
means for selecting one of said plurality of current levels as a function of said detected battery voltage.

43. The implantable medical device according to claim 42 wherein said current level selecting means comprises
means for defining a series of voltage ranges and
means for selecting a particular current level whenever said detected battery voltage falls within a particular one of said voltage ranges.

44. The implantable medical device according to claim 43 wherein said therapy delivering means comprise a cardiac pacemaker.

45. The implantable medical device according to claim 43 wherein said therapy delivering means comprise a cardiac defibrillator.

46. An implantable medical device comprising
means for delivering a therapy to the body of a patient,
means in electrical communication with said therapy delivering means for controlling said therapy delivering means, and
an electrical power supply having
a rechargeable battery in electrical communication with said therapy delivering means and said controlling means,
means for receiving a charge for said battery from a power source external to the body of a patient, said charge receiving means being connected to said battery,
means in electrical communication with said battery for periodically detecting a battery voltage of said battery,
means in electrical communication with said charge receiving means for regulating a recharging current being delivered to said battery during charging to a plurality of predetermined current levels,
means in electrical communication with said voltage detecting means and said current regulating means for selecting one of said plurality of current levels as a function of said detected battery voltage, and
means in electrical communication with said detecting means and said charge receiving means for terminating charging whenever said voltage exceeds a predetermined level.

47. The implantable medical device according to claim 46 wherein said current level selecting means comprises
means for defining a series of voltage ranges and
means for selecting a particular current level whenever said detected battery voltage falls within a particular one of said voltage ranges.

48. The implantable medical device according to claim 47 wherein said therapy delivering means comprise a cardiac pacemaker.

49. The implantable medical device according to claim 47 wherein said therapy delivering means comprise a cardiac defibrillator.

* * * * *